(12) United States Patent
Ishii et al.

(10) Patent No.: US 7,038,064 B2
(45) Date of Patent: May 2, 2006

(54) PROCESS FOR PRODUCING HYDROXYLACTONES

(75) Inventors: Yasutaka Ishii, Takatsuki (JP); Tatsuya Nakano, Himeji (JP); Keizo Inoue, Himeji (JP)

(73) Assignee: Diacel Chemical Industries, Ltd., Osaka (JP)

( * ) Notice: Subject to any disclaimer, the term of this patent is extended or adjusted under 35 U.S.C. 154(b) by 379 days.

(21) Appl. No.: 10/332,049

(22) PCT Filed: Jul. 18, 2001

(86) PCT No.: PCT/JP01/06200

§ 371 (c)(1), (2), (4) Date: Jan. 6, 2003

(87) PCT Pub. No.: WO02/06262

PCT Pub. Date: Jan. 24, 2002

(65) Prior Publication Data

US 2004/0024228 A1 Feb. 5, 2004

(30) Foreign Application Priority Data

Jul. 19, 2000 (JP) .............................. 2000-219706

(51) Int. Cl.
*C07D 307/32* (2006.01)
*C07D 309/30* (2006.01)

(52) U.S. Cl. ...................................... 549/292; 549/313

(58) Field of Classification Search ................ 549/292, 549/313

See application file for complete search history.

(56) References Cited

FOREIGN PATENT DOCUMENTS

JP    2000-159693 A    6/2000

OTHER PUBLICATIONS

Tan et al., Journal of Molecular Catalysis A: Chemical 142 (1999) pp. 333-338.

*Primary Examiner*—Cecilia J. Tsang
*Assistant Examiner*—Raymond Covington
(74) *Attorney, Agent, or Firm*—Birch, Stewart, Kolasch & Birch, LLP

(57) ABSTRACT

A process of the present invention produces a hydroxylactone by subjecting an unsaturated carboxylic acid having a double bond not conjugated to a carboxyl group or an ester thereof to (i) a reaction with hydrogen peroxide in the presence of a metallic compound containing a metallic element selected from W, Mo, V and Mn or (ii) a reaction with a peroxide containing the metallic element to thereby yield a corresponding hydroxylactone having a hydroxyl group combined with one of carbon atoms constituting the double bond and being cyclized at the other carbon atom position. The metallic compound may be one selected from oxides, oxoacids and salts thereof. The unsaturated carboxylic acid includes, for example, $\beta,\gamma$-unsaturated carboxylic acids, $\gamma,\delta$-unsaturated carboxylic acids, and $\delta,\epsilon$-unsaturated carboxylic acids. The process can produce hydroxylactones in high yields at low cost.

3 Claims, No Drawings

PROCESS FOR PRODUCING HYDROXYLACTONES

This application is the national phase under 35 U.S.C. § 371 of PCT International Application No. PCT/JP01/06200 which has an International filing date of Jul. 18, 2001, which designated the United States of America.

TECHNICAL FIELD

The present invention relates to a process for producing hydroxylactones. More specifically, it relates to a process for producing a corresponding hydroxylactone from an unsaturated carboxylic acid having a double bond not conjugated to a carboxyl group or an ester thereof.

BACKGROUND ART

Lactones having a hydroxyl group are useful compounds as materials for photosensitive resins and other functional polymers and as materials for pharmaceutical drugs, agricultural chemicals, and other fine chemicals.

Certain processes for producing lactones having a hydroxy group have been proposed. For example, Journal of Molecular Catalysis A: Chemical, 142 (1999), 333–338 proposes a process for producing a hydroxylactone in which a β,γ-unsaturated carboxylic acid, a γ,δ-unsaturated carboxylic acid, or a δ,ε-unsaturated carboxylic acid is allowed to react with hydrogen peroxide in the presence of methyltrioxorhenium and thereby yields a corresponding hydroxylactone. This process requires the use of expensive and toxic rhenium and is not industrially advantageous.

DISCLOSURE OF INVENTION

Accordingly, an object of the present invention is to provide an industrially advantageous process that can produce hydroxylactones in high yields at low cost.

After intensive investigations to achieve the above object, the present inventors have found that a corresponding hydroxylactone can be efficiently produced at low cost by allowing an unsaturated carboxylic acid having a double bond not conjugated to a carboxyl group or an ester thereof to react with a specific compound. The present invention has been accomplished based on these findings.

Specifically, the present invention provides a process for producing hydroxylactones, including the step of subjecting an unsaturated carboxylic acid having a double bond not conjugated to a carboxyl group or an ester thereof to (i) a reaction with hydrogen peroxide in the presence of a metallic compound containing a metallic element selected from W, Mo, V and Mn or (ii) a reaction with a peroxide containing the metallic element to thereby yield a corresponding hydroxylactone having a hydroxyl group combined with one of two carbon atoms constituting the double bond and being cyclized at the other carbon atom positon.

As the metallic compound, for example, at least one selected from oxides, oxoacids and salts thereof can be used. The unsaturated carboxylic acid includes, for example, β,γ-unsaturated carboxylic acids, γ,δ-unsaturated carboxylic acids, and δ,ε-unsaturated carboxylic acids.

The term "hydroxylactone(s)" as used herein means and includes not only compounds having a hydroxyl group directly combined with a lactone ring but also compounds having a hydroxyl-group-containing substituent combined with a lactone ring. The term "peroxide" is used in a broad sense and includes peroxoacids and salts thereof, peracids and salts thereof in addition to peroxides and hydroperoxides in the narrow sense.

BEST MODE FOR CARRYING OUT THE INVENTION

[Substrate]

Unsaturated carboxylic acids and esters thereof for use as a reaction material (substrate) in the present invention are not specifically limited as long as they are carboxylic acids having a double bond not conjugated to a carboxylic group and esters thereof.

Examples of such unsaturated carboxylic acids for use as the substrate include β,γ-unsaturated carboxylic acids represented by following Formula (1a), γ,δ-unsaturated carboxylic acids represented by following Formula (1b), and δ,ε-unsaturated carboxylic acids represented by following Formula (1c):

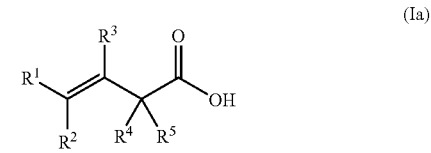
(1a)

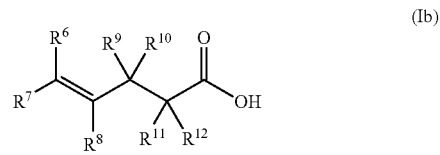
(1b)

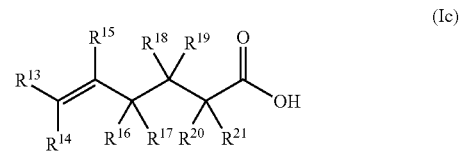
(1c)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and R21 are the same or different and are each a hydrogen atom or an organic group, and at least two of $R^1$ to $R^5$ in Formula (1a), $R^7$ to $R^{12}$ in Formula (1b) or $R^{13}$ to $R^{21}$ in Formula (1c) may be combined to form a ring with an adjacent carbon atom or carbon chain.

The organic group is not specifically limited as long as it is a group not adversely affecting the reaction. Such organic groups include, but are not limited to, halogen atoms, hydrocarbon groups, heterocyclic groups, substituted oxycarbonyl groups (e.g., alkoxycarbonyl groups, aryloxycarbonyl groups, aralkyloxycarbonyl groups, and cycloalkyloxycarbonyl groups), carboxyl group, substituted or unsubstituted carbamoyl groups, (N-substituted or unsubstituted amido groups), cyano group, nitro group, sulfur acid groups (sulfonic groups and sulfinic groups), sulfur acid ester groups (sulfonic ester groups and sulfinic ester groups), acyl groups, hydroxyl group, alkoxy groups, and N-substituted or unsubstituted amino groups. The carboxyl group, hydroxyl group, and amino groups may be protected by a conventional protective group.

The halogen atoms include fluorine, chlorine, bromine, and iodine atoms. The hydrocarbon groups include aliphatic hydrocarbon groups, alicyclic hydrocarbon groups, and aromatic hydrocarbon groups. The aliphatic hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups, and alkynyl groups) each containing from about 1 to about 20 carbon atoms, preferably from about 1 to about 10 carbon atoms, and more preferably from about 1 to about 6 carbon atoms.

The alicyclic hydrocarbon groups include, but are not limited to, cyclopropyl, cyclobutyl, cyclopentyl, cyclohexyl, cyclohexenyl, cyclooctyl, cyclodecyl, cyclododecyl, and other alicyclic hydrocarbon groups (e.g., cycloalkyl groups and cycloalkenyl groups) each containing from about 3 to about 20 carbon atoms, and preferably form about 3 to about 15 carbon atoms. The aromatic hydrocarbon groups include, for example, phenyl, naphthyl, and other aromatic hydrocarbon groups each containing from about 6 to about 14 carbon atoms.

These hydrocarbon groups may have a substituent. Such substituents include, but are not limited to, halogen atoms (fluorine, chlorine, bromine, and iodine atoms), oxo group, hydroxyl group which may be protected by a protective group, hydroxymethyl group which may be protected by a protective group, amino groups which may be protected by a protective group, carboxyl group which may be protected by a protective group, substituted oxycarbonyl groups, substituted or unsubstituted carbamoyl groups, nitro group, acyl groups, cyano group, alkyl groups such as methyl, ethyl and other $C_1$–$C_4$ alkyl groups, cycloalkyl groups, aryl groups such as phenyl and naphthyl groups, and heterocyclic groups. Conventional protective groups in the field of organic synthesis can be used as the protective groups.

Heterocyclic rings constituting the heterocyclic groups include aromatic heterocyclic rings and non-aromatic heterocyclic rings. Such heterocyclic rings include, for example, 5-or 6-membered heterocyclic rings containing at least one atom selected from oxygen, sulfur, and nitrogen atoms as a hetero atom. The heterocyclic rings may be condensed rings and may have a substituent (a similar group to those which the hydrocarbon groups may have).

The alkoxycarbonyl groups include, but are not limited to, methoxycarbonyl, ethoxycarbonyl, and other $C_1$–$C_6$ alkoxycarbonyl groups. The aryloxycarbonyl groups include, but are not limited to, phenyloxycarbonyl group. The aralkyloxycarbonyl groups include, for example, benzyloxycarbonyl group. The cycloalkyloxycarbonyl groups include, for example, cyclopentyloxycarbonyl and cyclohexyloxycarbonyl groups. The substituted carbamoyl groups include, for example, N-methylcarbamoyl and N,N-dimethylcarbamoyl groups. The sulfonic ester groups include, for example, methyl sulfonate, ethyl sulfonate, and other sulfonic acid $C_1$–$C_4$ alkyl ester groups. The sulfinicester groups include methyl sulfinate, ethyl sulfinate, and other sulfinic acid $C_1$–$C_4$ alkyl ester groups. The acyl groups include, but are not limited to, acetyl, propionyl, and other aliphatic acyl groups (e.g., $C_2$–$C_7$ aliphatic acyl groups), benzoyl and other aromatic acyl groups. The alkoxy groups include, but are not limited to, methoxy, ethoxy, propoxy, butoxy, and other alkoxy groups each containing from about 1 to about 6 carbon atoms. The N-substituted amino groups include, but are not limited to, N,N-dimethylamino, N,N-diethylamino, and piperidino groups.

Preferred organic groups include, for example, hydrogen atom; methyl, ethyl, propyl, isopropyl, butyl, isobutyl, s-butyl, t-butyl, pentyl, hexyl, and other $C_1$–$C_{10}$ alkyl groups (especially, $C_1$–$C_4$ alkyl groups); cyclopentyl, cyclohexyl, and other $C_3$–$C_{15}$ alicyclic hydrocarbon groups; and phenyl, and other aromatic hydrocarbon groups.

At least two of $R^1$ to $R^5$ in Formula (1a), $R^7$ to $R^{12}$ in Formula (1b) or $R^{13}$ to $R^{21}$ in Formula (1c) may be combined to form a ring with an adjacent carbon atom or carbon chain. Such rings include, but are not limited to, cyclopropane ring, cyclobutane ring, cyclopentane ring, cyclopentene ring, cyclohexane ring, cyclohexene ring, cyclooctane ring, cyclododecane ring, and other cycloalkane rings and cycloalkene rings each containing from about 3 to about 20 members; norbornane ring, norbornene ring, adamantane ring, decalin ring, perhydrofluorene ring, tricyclo[5.2.1.0$^{2,6}$]decane ring, and other bridged rings.

These groups may have a substituent such as a similar group to those which the hydrocarbon groups may have. Another ring (a non-aromatic ring or aromatic ring) may be condensed with each of these rings.

Examples of the β,γ-unsaturated carboxylic acids represented by Formula (1a) include, but are not limited to, 3-butenoic acid, 3-pentenoic acid, 3-hexenoic acid, 3-methyl-3-butenoic acid, 2-methyl-3-butenoic acid, and 2,2-dimethyl-3-butenoic acid.

Examples of the γ,δ-unsaturated carboxylic acids include, but are not limited to, 4-pentenoic acid, 4-hexenoic acid, 4-heptenoic acid, 4-methyl-4-pentenoic acid, 3-methyl-4-pentenoic acid, 3,3-dimethyl-4-pentenoic acid, 2-methyl-4-pentenoic acid, 2,2-dimethyl-4-pentenoic acid, 2,3-dimethyl-4-pentenoic acid, cyclopentene-3-acetic acid, cyclohexene-3-acetic acid, and 5-norbornene-2-carboxylic acid.

Examples of the δ,ε-unsaturated carboxylic acids include, but are not limited to, 5-hexenoic acid, 5-heptenoic acid, 5-octenoic acid, 5-methyl-5-hexenoic acid, 4-methyl-5-hexenoic acid, 4,4-dimethyl-5-hexenoic acid, 3-methyl-5-hexenoic acid, 3,3-dimethyl-5-hexenoic acid, 2-methyl-5-hexenoic acid, 2,2-dimethyl-5-hexenoic acid, 3,4-dimethyl-5-hexenoic acid, 2,4-dimethyl-5-hexenoic acid, 2,3-dimethyl-5-hexenoic acid, and 2,3,4-trimethyl-5-hexenoic acid.

Esters of the unsaturated carboxylic acids include, but are not limited to, methyl esters, ethyl esters, propyl esters, isopropyl esters, butyl esters, isobutyl esters, s-butyl esters, t-butyl esters, and other alkyl esters (e.g., $C_1$–$C_4$ alkyl esters); cyclohexyl esters, and other cycloalkyl esters; phenyl esters, and other aryl esters; benzyl esters, and other aralkyl esters.

[Metallic Compounds]

According to the present invention, the unsaturated carboxylic acid or an ester thereof is subjected to (i) a reaction with hydrogen peroxide in the presence of a metallic compound containing a metallic element selected from W, Mo, V, and Mn or (ii) a reaction with a peroxide containing the metallic element.

The metallic compounds in the reaction (i) are not specifically limited, as long as they are compounds containing a metallic element selected from W, Mo, V, and Mn, and include, for example, oxides, oxoacids and salts thereof, sulfides, halides, oxyhalides, borides, carbides, silicides, nitrides, phosphides, peroxides, complexes (inorganic complexes and organic complexes), and organometallic compounds each containing the metallic element. Each of these metallic compounds can be used alone or in combination.

The oxides include, but are not limited to, tungsten oxides such as $WO_2$ and $WO_3$, molybdenum oxides such as $MoO_2$ and $MoO_3$, vanadium oxides such as $VO$, $V_2O_3$, $VO_2$, and $V_2O_5$, manganese oxides such as $MnO$, $Mn_2O_3$, $Mn_3O_4$, $MnO_2$, and $Mn_2O_7$, and complex oxides containing any of the metals.

The oxoacids include, but are not limited to, tungstic acid, molybdic acid, vanadic acid, and manganic acid, as well as isopolytungstic acid, isopolymolybdic acid, isopolyvanadic acid, and other isopolyacids; phosphotungstic acid, silicotungstic acid, phosphomolybdic acid, silicomolybdic acid, phosphovanadomolybdic acid, and other heteropolyacids each comprising the metallic element and other metallic element(s) Preferred examples of such other metallic elements in the heteropolyacids are phosphorus and silicon, of which phosphorus is typically preferred.

The salts of oxoacids include, but are not limited to, sodium salts, potassium salts, and other alkali metal salts; magnesium salts, calcium salts, barium salts, and other alkaline earth metal salts; ammonium salts; and transition metal salts, of the oxoacids. The salts of oxoacids such as salts of heteropolyacids may be salts except with another cation replacing part of hydrogen atoms corresponding to a cation.

The peroxides include, but are not limited to, peroxides; hydroperoxides; peroxoacids such as peroxotungstic acid, peroxomolybdic acid, and peroxovanadic acid; salts of peroxoacids such as alkali metal salts, alkaline earth metal salts, ammonium salts, and transition metal salts of the peroxoacids; peracids such as permanganic acid; and salts of peracids such as alkali metal salts, alkaline earth metal salts, ammonium salts, and transition metal salts of the peracids.

The amount of the metallic compound is, for example, from about 0.0001 to about 2 moles, preferably from about 0.0005 to about 0.5 mole, and more preferably from about 0.001 to about 0.2 mole per mole of the unsaturated carboxylic acid or an ester thereof used in the reaction.

The active species in the reaction (i) is supposed to be the peroxide containing the metal or a peroxy radical.

The peroxide in the reaction (ii) includes those as mentioned above. Each of these peroxides can be used alone or in combination. The amount of the peroxide is, for example, from about 0.8 to about 2 moles, preferably from about 0.9 to about 1.5 moles, and more preferably from about 0.95 to 1.2 moles per mole of the unsaturated carboxylic acid or an ester thereof used in the reaction. [Hydrogen Peroxide]

Hydrogen peroxide used herein may be pure hydrogen peroxide but is generally a diluted hydrogen peroxide in an appropriate solvent such as water (e.g., 30% by weight hydrogen peroxide aqueous solution) for handleability.

The amount of hydrogen peroxide is, for example, from about 0.9 to about 5 moles, preferably from about 0.9 to about 3 moles, and more preferably from about 0.95 to about 2 moles per mole of the unsaturated carboxylic acid or an ester thereof used in the reaction.

[Reactions]

The reaction is performed in the presence of, or in the absence of, a solvent. Such solvents include, but are not limited to, t-butyl alcohol, and other alcohols; chloroform, dichloromethane, 1,2-dichloroethane, and other halogenated hydrocarbons; benzene, and other aromatic hydrocarbons; hexane, heptane, octane, and other aliphatic hydrocarbons; cyclohexane, and other alicyclic hydrocarbons; N,N-dimethylformamide, N,N-dimethylacetamide, and other amides; acetonitrile, propionitrile, benzonitrile, and other nitriles; ethyl ether, tetrahydrofuran, and other chain or cyclic ethers; ethyl acetate, and other esters; acetic acid, and other organic acids; and water. Each of these solvents can be used alone or in combination.

A reaction temperature can be appropriately selected in consideration of the rate and selectivity of the reaction and is generally from about 0° C. to about 100° C., and preferably from about 10° C. to about 60° C. The reaction can be performed in any system such as batch system, semi-batch system, and continuous system.

The reaction yields a corresponding hydroxylactone having a hydroxyl group combined with one of carbon atoms constituting the double bond of the material unsaturated carboxylic acid and being cyclized at the other carbon atom position. In the reaction, it is supposed that the double bond is initially epoxidized, an intramolecular cyclization reaction accompanied with ring-opening of the epoxy ring then proceeds and thereby yields the corresponding hydroxylactone.

At which carbon atom position of two carbon atoms constituting the double bond the cyclization occurs is determined depending on the electrical properties and bulkiness of substituent(s) combined with the carbon atom, steric regulation, stability of the produced lactone, and other conditions. When an unsaturated carboxylic acid having a ring containing at least two carbon atoms between the carbon atom at the alpha-position of the carboxyl group and a distal carbon atom constituting the double bond or its ester is used as the substrate, a polycyclic compound having the ring condensed with the lactone ring can be produced.

More specifically, the β,γ-unsaturated carboxylic acids represented by Formula (1a) or esters thereof generally yield, for example, β-hydroxy-γ-butyrolactone derivatives represented by following Formula (2a):

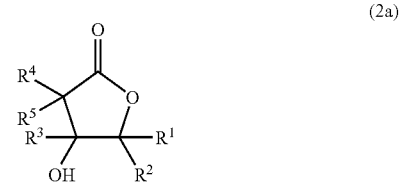

(2a)

wherein $R^1$, $R^2$, $R^3$, and $R^4$ have the same meanings as defined above. For example, by using 3-butenoic acid or an ester thereof as a material, β-hydroxy-γ-butyrolactone (4-hydroxydihydrofuran-2-one) can be obtained in a high yield.

The γ,δ-unsaturated carboxylic acids represented by Formula (1b) or esters thereof generally yield γ-hydroxymethyl-γ-butyrolactone derivatives represented by following Formula (2b-1), and some of them yield γ-hydroxy-δ-valerolactone derivatives represented by following Formula (2b-2):

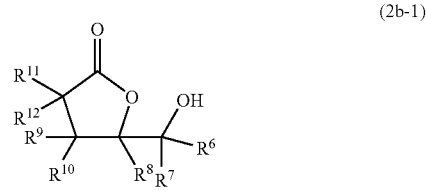

(2b-1)

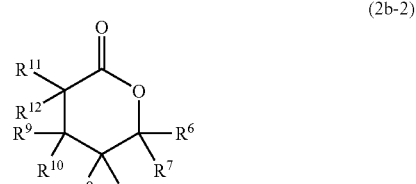

(2b-2)

wherein $R^6$, $R^7$, $R^8$, $R^9$, $R^{10}$, $R^{11}$, and $R^{12}$ have the same meanings as defined above.

For example, 4-pentenoic acid or an ester thereof yields γ-hydroxymethyl-γ-butyrolactone (5-hydroxymethyldihydrofuran-2-one) in a high yield. Cyclopentene-3-acetic acid yields 2,3-dihydroxycyclopentaneacetic acid γ-lactone, and 5-norbornene-2-carboxylic acid yields 5,6-dihydroxybicyclo[2.2.1]octane-2-carboxylic acid γ-lactone (5-hydroxy-2,6-norbornanecarbolactone=5-hydroxy-3-oxatricyclo[4.2.1.0$^{4,8}$]nonan-2-one) in high yields.

The δ,ε-unsaturated carboxylic acids represented by Formula (1c) or esters thereof yield δ-hydroxymethyl-δ-valerolactone derivatives represented by following Formula (2c):

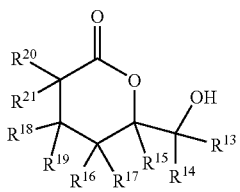

(2c)

wherein $R^{13}$, $R^{14}$, $R^{15}$, $R^{16}$, $R^{17}$, $R^{18}$, $R^{19}$, $R^{20}$, and $R^{21}$ have the same meanings as defined above. Some of these substrates yield ε-caprolactone derivatives. For example, 5-hexenoic acid yields δ-hydroxymethyl-δ-valerolactone (6-hydroxymethyltetrahydropyran-2-one) in a high yield.

When an ester of the unsaturated carboxylic acid is used as the substrate, an alcohol corresponding to the ester is by-produced. Reaction products can be easily separated and purified by conventional separation means such as filtration, concentration, distillation, extraction, crystallization, recrystallization, column chromatography, and combinations thereof.

INDUSTRIAL APPLICABILITY

The hydroxylactones thus obtained can be used as materials for photosensitive resins and other functional materials and as materials for pharmaceutical drugs, agricultural chemicals, and other fine chemicals.

The process of the present invention can produce such hydroxylactones in high yields at low cost and is therefore very advantageous for commercial production of hydroxylactones.

EXAMPLES

The present invention will be illustrated in further detail with reference to several examples below, which are not intended to limit the scope of the invention.

Example 1

A total of 2 ml of 30% by weight hydrogen peroxide aqueous solution was added dropwise to a stirred mixture of 1.38 g (10 mmol) of 5-norbornene-2-carboxylic acid, 25 mg (0.1 mmol) of tungstic acid, and 15 ml of t-butyl alcohol at room temperature, followed by stirring at 40° C. for 3 hours. As a result, 5-hydroxy-2,6-norbornanecarbolactone (i.e., 5-hydroxy-3-oxatricyclo[4.2.1.0$^{4,8}$]nonan-2-one) represented by the following formula was produced in a yield of 82% with a conversion from 5-norbornene-2-carboxylic acid of 95%.

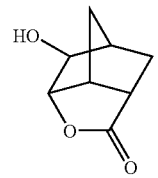

Example 2

A total of 2 ml of 30% by weight hydrogen peroxide aqueous solution was added dropwise to a stirred mixture of 1.38 g (10 mmol) of 5-norbornene-2-carboxylic acid, 16.2 mg (0.1 mmol) of molybdic acid, and 15 ml of t-butyl alcohol at room temperature, followed by stirring at 40° C. for 5 hours. As a result, 5-hydroxy-2, 6-norbornanecarbolactone was produced in a yield of 85% with a conversion from 5-norbornene-2-carboxylic acid of 99%.

Example 3

A total of 2 ml of 30% by weight hydrogen peroxide aqueous solution was added dropwise to a stirred mixture of 1.38 g (10 mmol) of 5-norbornene-2-carboxylic acid, 50 mg (0.2 mmol) of tungstic acid, and 15 ml of chloroform at room temperature, followed by stirring at room temperature for 5 hours. As a result, 5-hydroxy-2,6-norbornanecarbolactone was produced in a yield of 5% with a conversion from 5-norbornene-2-carboxylic acid of 11%.

Example 4

A total of 2 ml of 30% by weight hydrogen peroxide aqueous solution was added dropwise to a stirred mixture of 0.86 g (10 mmol) of 3-butenoic acid, 25 mg (0.1 mmol) of tungstic acid, and 15 ml of t-butyl alcohol at room temperature, followed by stirring at 70° C. for 6 hours. As a result, β-hydroxy-γ-butyrolactone was produced in a yield of 91%.

Example 5

A total of 2 ml of 30% by weight hydrogen peroxide aqueous solution was added dropwise to a stirred mixture of 1.00 g (10 mmol) of 4-pentenoic acid, 25 mg (0.1 mmol) of tungstic acid, and 15 ml of t-butyl alcohol at room temperature, followed by stirring at 70° C. for 10 hours. As a result, γ-hydroxymethyl-γ-butyrolactone was produced in a yield of 88%.

Example 6

A total of 2 ml of 30% by weight hydrogen peroxide aqueous solution was added dropwise to a stirred mixture of 1.12 g (10 mmol) of 5-hexenoic acid, 25 mg (0.1 mmol) of tungstic acid, and 15 ml of t-butyl alcohol at room temperature, followed by stirring at 70° C. for 8 hours. As a result, δ-hydroxymethyl-δ-valerolactone was produced in a yield of 72%.

Example 7

A total of 14.7 g (130 mmol) of 30% by weight hydrogen peroxide aqueous solution was added dropwise to a mixture of 13.8 g (100 mmol) of 5-norbornene-2-carboxylic acid, 1.25 g (5 mmol) of tungstic acid, and 60 ml of water over 30 minutes while controlling the inside temperature within a range from 43° C. to 47° C., followed by stirring at 50° C. for 4.5 hours. After standing to cool to room temperature, the reaction mixture was diluted with 10% by weight sodium sulfite aqueous solution and was concentrated using a rotary evaporator. The concentrate was treated with ethyl acetate and 10% by weight sodium carbonate aqueous solution for separation. The ethyl acetate layer was concentrated and was then diluted with hexane. The precipitated crystal was filtrated, was dried and thereby yielded 5-hydroxy-2,6-norbornanecarbolactone in a yield of 52%.

Example 8

A total of 6.5 g of 30% by weight hydrogen peroxide aqueous solution was added dropwise to a mixture of 6.9 g (50 mmol) of 5-norbornene-2-carboxylic acid, 0.94 g (3.76 mmol) of tungstic acid, 0.92 g (11.2 mmol) of sodium acetate, and 20 g of t-butyl alcohol at 43° C. to 47° C. over 30 minutes, followed by stirring at 50° C. for 5.5 hours. As a result, 5-hydroxy-2,6-norbornanecarbolactone was produced in a yield of 26% with a conversion from 5-norbornene-2-carboxylic acid of 52%.

The invention claimed is:

1. A process for producing hydroxylactones, comprising the step of:

subjecting an unsaturated carboxylic acid having a double bond not conjugated to a carboxyl group or an ester thereof to (i) a reaction with hydrogen peroxide in the presence of a metallic compound containing a metallic element selected from W, Mo, V and Mn or (ii) a reaction with a peroxide containing the metallic element to thereby yield a corresponding hydroxylactone having a hydroxyl group combined with one of two carbon atoms constituting the double bond and being cyclized at the other carbon atom position.

2. The process for producing hydroxylactones according to claim 1, wherein the metallic compound is at least one selected from oxides, oxoacids and salts thereof.

3. The process for producing hydroxylactones according to claim 1, wherein the unsaturated carboxylic acid is one of β,γ-unsaturated carboxylic acids, γ,δ-unsaturated carboxylic acids, and δ,ε-unsaturated carboxylic acids.

* * * * *

UNITED STATES PATENT AND TRADEMARK OFFICE
CERTIFICATE OF CORRECTION

| | | |
|---|---|---|
| PATENT NO. | : 7,038,064 B2 | Page 1 of 1 |
| APPLICATION NO. | : 10/332049 | |
| DATED | : May 2, 2006 | |
| INVENTOR(S) | : Yasutaka Ishii et al. | |

It is certified that error appears in the above-identified patent and that said Letters Patent is hereby corrected as shown below:

On the cover page item "(73) Assignee" should read:

-- (73) Assignee: Daicel Chemical Industries, Ltd., --

Signed and Sealed this

First Day of May, 2007

JON W. DUDAS
*Director of the United States Patent and Trademark Office*